United States Patent [19]

Feinstein et al.

[11] 4,142,036

[45] Feb. 27, 1979

[54] POLYPHENYLCARBOXYLIC ACID ADAMANTANE COMPOUNDS AND POLYMERS PREPARED THEREFROM

[75] Inventors: Allen I. Feinstein, Wheaton; Ellis K. Fields, River Forest, both of Ill.

[73] Assignee: Standard Oil Company (Indiana), Chicago, Ill.

[21] Appl. No.: 691,772

[22] Filed: Jun. 1, 1976

[51] Int. Cl.$^2$ .................. C08G 63/18; C08G 63/66; C08G 69/26; C08G 69/32

[52] U.S. Cl. .............................. 528/183; 260/346.3; 260/346.4; 528/173; 528/190; 528/188; 528/296; 528/298; 528/337; 528/342; 528/344; 528/350; 528/352; 528/353; 560/80; 562/488

[58] Field of Search ......... 260/515 P, 475 FR, 475 R, 260/346.3, 346.4, 47 C, 49, 75 R, 78 R, 75 S, 78 TF, 47 CP

[56] References Cited

U.S. PATENT DOCUMENTS

| | | | |
|---|---|---|---|
| 1,721,560 | 7/1929 | Kalischer et al. | 260/515 P |
| 3,678,072 | 7/1972 | Klanderman et al. | 260/326.5 B |
| 3,720,701 | 3/1973 | Klanderman et al. | 260/475 FR |

*Primary Examiner*—Lester L. Lee
*Attorney, Agent, or Firm*—William C. Clarke; Arthur G. Gilkes; William T. McClain

[57] ABSTRACT

Adamantane compounds having 2 to 4 bridgehead positions substituted with phenylacyl moieties are prepared by oxidizing poly(phenylalkyl) adamantanes. The polyacyl adamantane compounds are useful as intermediates for polyesters, polyamides and polyimides. The esters are useful as plasticizers for polyvinylchloride.

27 Claims, No Drawings

POLYPHENYLCARBOXYLIC ACID ADAMANTANE COMPOUNDS AND POLYMERS PREPARED THEREFROM

The field of this invention relates to adamantane compounds having 2 to 4 bridgehead positions substituted with phenylacyl moieties suitable for producing polymers useful for forming shaped objects, such as film, fiber, and molded parts. The esters are also suitable as plasticizers for polyvinylchloride and other polymers.

The highly symmetrical molecule of adamantane possesses six secondary carbons and four tertiary (bridgehead) carbons, the ten carbon atoms being arranged in a completely symmetrical, strainless manner. The four bridgehead carbons which are equivalent to each other are more susceptible to attack than the secondary carbons. The relative ease of the bridgehead carbons to react permits a carbonium ion process to occur with facility. Functional groups are introduced sequentially with ease into the bridgehead positions designated by the numerals 1, 3, 5 and 7 respectively in the following typographical representation:

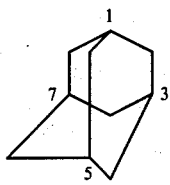

A single substituted product is easiest. A di-substituted product is always in the 1-3 bridgehead positions. A tri-substituted product is always in the 1-3-5 bridgehead positions. A tetra-substituted product is always in the 1-3-5-7 positions.

As is well known, the mechanical and physical properties of a fiber or film depend on the chemical structure of the polymer from which it is made. For example, the melting point, molding temperature, and glass transition temperature of the polymer composition control many of the physical properties and fabrication of the shaped objects. The melting point determines thermal resistance and heat-setting temperature of fibers. Molding temperature determines fabrication temperature. Glass transition temperature (Tg) determines initial modulus, tensile strain recovery, work of recovery, drape and hand, wash-and-wear characteristics, comfort factors and resilience of fibers. The main molecular factors which influence these properties include chain stiffness, the intermolecular forces, orientation and crystallinity.

Accordingly, there has been considerable interest in developing aromatic acids as precursors for thermally stable polymers, such as polyesters or polyamides. It is well known that the introduction of aromatic units in the polymer chain backbone results in high bond energies, a low degree of reactivity, and rigidity of the polymer chain structure. The use of aliphatic units in the polymer chain backbone results in flexibility, lower temperature characteristics and decreased strength as compared with the aromatic types.

Substantially all commercial polyester fibers are based on terephthalic acid. While these fibers have many excellent properties there is a need for polyester fibers having a higher Tg than provided by terephthalic acid polyesters. Recently, 2,6-naphthalene dicarboxylic acid has been proposed as a suitable aromatic acid for producing polyesters suitable for tire cord. This acid provides polyesters having a higher Tg than those based on terephthalic acid. For example, poly(ethylene terephthalate) has a Tg of 74° C. while poly(ethylene 2,6-naphthalate) has a Tg of 115°–125° C. However, the difficulties of manufacturing the precursor, i.e., 2,6-dimethylnaphthalene, have made the production of this acid technically difficult and economically costly. The acid can require a four-step synthesis with attendant loss in yield and consequent high cost.

Various other organic polymers have been suggested for use as high temperature fibers, such as copolyamides (Kevlar), polybenzimidiazoles, polyoxadiazoles, polyimides and phenylene ring systems (polyphenylenes). Polyarylates and polycarbonates have been suggested for use as engineering plastics. However, all of these are costly and/or difficult to manufacture. Accordingly, there is a need for new aromatic acids suitable for preparing polymers for many uses.

The substituted adamantane nucleus when incorporated into a polymer is known to be capable of providing unique physical properties. For example, the geometric bulk of 1,3-dimethyladamantane in its polymers results in rigidity, high thermal stability, high glass transition temperatures, low crystallinity, high heat-distortion temperatures, and good hydrolytic stability. Good oxidative stability results from the absence of labile ring hydrogens.

It is therefore the general object of this invention to provide a new group of aromatic polycarboxylic acids incorporating the adamantane nucleus and provide a process for making these acids. A specific object of this invention is to provide new adamantane polyphenylcarboxylic acids wherein the carboxy groups are in the 3, 4, 5 positions on the phenyl rings. 1,3-di(4-carboxyphenyl)adamantane, 1,3-di(3,4-dicarboxyphenyl)adamantane and 1,3-di(3,5-dicarboxyphenyl)adamantane are among the novel acids provided. A further object is to provide novel adamantane polymers, such as polyamides, polyesters and polyimides, made from these acid compounds (acids, acyl halides, simple esters, e.g., methyl, etc.). An additional object is to provide esters of these acids and monohydric alcohols containing 1 to 24 carbon atoms which can be used as plasticizers for polyvinylchloride (PVC).

Surprisingly, it has been found that adamantane polyphenylcarboxylic acid compounds can be prepared in a very convenient manner by the controlled oxidation of polyalkylphenyl adamantanes.

It has been found also that some of the linear polyesters of this invention unexpectedly have high second order transition temperatures (Tg). For example, the glass transition temperature (Tg) of the 1,3-di(4-carboxyphenyl)adamantane and ethylene glycol polyester is 138° C. As a comparison, the Tg of polyethylene terephthalate is approximately 74°–78° C.

The use of an oxidative technique upon aromatic alkyl adamantanes to oxidize the alkyl moiety of the molecule has not been reported previously in the prior art although oxidative techniques have been used on the adamantane nucleus itself. Based on the prior art, oxidation of a phenyladamantane would be expected to give a phenyl hydroxy adamantane on which the hydroxyl group is located at one of the bridgehead positions of the adamantane ring. Schneider, U.S. Pat. No. 3,356,740, dated Dec. 5, 1967, discloses the preparation of 1-hydroxy alkyladamantanes by oxidizing a bridgehead hydrogen by an oxygen-containing gas using a soluble metallic organic salt as catalyst. Moore, U.S.

Pat. No. 3,383,424, dated May 14, 1968 shows the preparation of hydroxy adamantane and hydroxy alkyl adamantanes by oxidation. Chromic acid in aqueous acetic acid is used to produce the monools or diols of adamantanes or alkyladamantanes.

SUMMARY OF THE INVENTION

Novel polyphenylcarboxylic acid adamantane compounds are prepared of the general formula

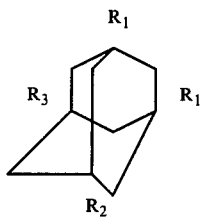

wherein each $R_1$ is selected from the group consisting of

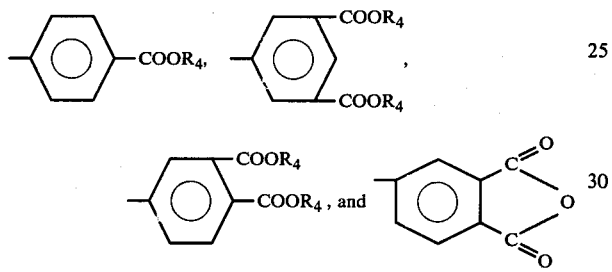

$R_2$ and $R_3$ are the same as $R_1$ or hydrogen, an alkyl radical of 1 to 4 carbon atoms, a phenyl radical, a biphenyl radical and a naphthyl radical, $R_4$ is hydrogen or an alkyl group of 1 to 24 carbon atoms. The acids are prepared by oxidizing poly(phenylalkyl)adamantanes.

The condensation polymers of this invention (the polyesters, polyamides and polyimides) are particularly useful for making coatings and shaped articles such as films and molded parts for use at elevated temperatures. The compounds having two acyl groups when reacted with dihydric alcohols, such as those having two to ten carbon atoms, form linear polyesters suitable for film and fiber applications. The polyacids or anhydrides having two ortho acyl groups on each phenyl ring are useful polyimide precursors. The monohydric alcohol esters, the alcohols being of 1 to 24 carbon atoms, of the adamantane compounds can be used as plasticizers for polyvinylchloride (PVC).

DESCRIPTION OF THE INVENTION

The polyphenylalkyl adamantane precursors useful in this invention can be produced by any one of several methods but in general two preparative techniques exist, both utilizing bromine compounds. Treatment of adamantane with bromine produces a single crystalline monobromide in excellent yield. As is well-known, by proper choice of Lewis catalyst and severity of conditions, such as refluxing with $Br_2$, $BBr_3$-$Br_2$, and $AlBr_3$-$Br_2$ at temperatures to 140° C., one to four bromines can be introduced sequentially into the adamantane molecule. Arylated adamantane compounds can be produced by reacting a bromoadamantane with an excess of an aromatic compound in a procedure such as that shown by Stetter et al., Chem. Ber. 97 (12) 3488-92 (1964). A hydroxyadamantane which can be derived from the bromine derivatives can also be used as the starting material. A typical preparation uses the 1,3-dihydroxy derivative of adamantane. This can be prepared from the 1,3-dibromoadamantane by the procedure given by H. Stetter and C. Wulff, Chem. Ber., 93, 1366 (1960) which uses an excess of dioxane.

Other methods are available also to produce the 1,3-dihydroxy derivative. Adamantane, as is noted in J. Org. Chem., 26, 2207-2212, (1961), has been oxidized by means of air to product 1-hydroxyadamantane as the principal oxidation product. Upon treatment of 1-hydroxyadamantane with 70% sulfuric acid according to the procedure of Geluk et al., as reported in Tetrahedron, 24, 5369 (1968), equimolar amounts of adamantane and 1,3-dihydroxyadamantane can be isolated in good yield.

In the practice of the invention, the alkylated aryl adamantanes are oxidized to the corresponding acids and converted directly to esters. In the case where the acids are dibasic in ortho positions, the acidic product is converted to the dianhydride. Two oxidative techniques can be used of which the second is preferable because of greater yield.

In the first technique, the reaction is a liquid phase oxidation process using a dichromate oxidation, the dichromate being selected from the group consisting of sodium dichromate, potassium dichromate and ammonium dichromate, preferably sodium dichromate. The ratio of sodium dicharomate relative to the hydrocarbon can be in the range of 3 to 10 moles, preferably 5 to 10 moles, of chromate ion per mole of substituted adamantane.

In one manner of carrying out the chromate oxidation, the dichromate is dissolved in water. The adamantane hydrocarbon is then introduced into the solution in which it is essentially insoluble. The mixture is agitated and heated whereby a mildly exothermic reaction occurs. The reaction can be effected by agitating the mixture of any temperature within the range of 230° to 300° C. The reaction is run in an autoclave at a pressure which maintains the reaction in the liquid phase at such temperature range. The reaction mixture is cooled and filtered to remove the chromium oxide. Acidification of the aqueous solution gives the acid as a precipitate.

In the second technique, the reaction is a liquid phase oxidation process using molecular oxygen catalyzed by the conjoint presence of a metal and bromine, as is taught in U.S. Pat. No. 2,833,816 which is incorporated by reference. In this technique which employs an organic acid solvent and a catalyst comprising at least one transition metal with a source of bromine to enhance the catalytic effect of the transition metal ion, the adamantane compound is reacted with an oxygen-containing gas (oxygen, air, etc.) at an elevated temperature within about the range of 75° to 150° C. and one to five atmospheres, preferably within the range of 100° to 150° C. and at a pressure to maintain the solvent in the liquid phase. The ratio of total oxygen fed into the reaction mixture relative to the hydrocarbon is in the range of about 2 to 500 moles of oxygen per mole of substituted adamantane, desirably in the range of 5 to 300, and preferably in the range of 5 to 75. The organic acid salts of cobalt and manganese are preferred catalysts.

The medium or solvent in which the oxidation process can be carried out can be any organic acid in which the adamantane compound is soluble, desirably the organic acid is a lower aliphatic monocarboxylic acid containing 1 to 8 carbon atoms in the molecule, said acid being in the liquid phase, preferably being saturated and containing 2 to 4 carbon atoms in the molecule, preferably being acetic acid and preferably employing about 0.1 to 100 parts by weight of such acid per part by weight of adamantane compound.

The monohydric alcohol esters of the adamantane polyphenylcarboxylic acid compounds of my invention are useful as plasticizers of polyvinylchloride and other polymer formulations. Suitable monohydric alcohols useful for producing the ester include aromatic or aliphatic, straight or branched chain, substituted or unsubstituted compounds of from 1 to 24 carbon atoms. Examples are alcohols such as methyl alcohol, ethyl alcohol, propyl alcohol, butyl alcohol, isobutyl alcohol, 2-ethyl hexyl alcohol, amyl alcohol, hexyl alcohol, cyclohexyl alcohol, heptyl alcohol, dodecyl alcohol, octyl alcohol, isotridecyl alcohol, stearyl alcohol, oleyl alcohol, tetracosyl alcohol, as well as aromatic hydroxy compounds containing from 6 to 24 carbon atoms such as phenol, naphthol, cresol, para-stearylphenol, etc.

These esters can be produced under conventional reaction conditions by reacting from about 1 to 10 moles of monohydroxy compound per carboxyl equivalent of said acid compound to form a solution of ester and monohydroxy compound. If desired, esterification catalysts or transesterification catalysts can be used, such as sulfuric acid, phosphoric acid, paratoluene sulfonic acid, benzene sulfonic acid, stannous octoate, boron trifluoride etherate, tetraalkyl titanates and zirconates of U.S. Pat. No. 3,056,818 etc.

The esters of monohydroxy compounds containing from 1 to 4 carbon atoms in each alkyl group can be used advantageously in ester interchange processes for producing high molecular weight polyesters while the esters containing from 1 to 24 carbon atoms in each ester moiety, preferably alkyl groups containing from about 4 to 13 carbon atoms, can be used as plasticizers for resinous polymers of vinyl chloride containing at least 50 mole percent vinyl chloride units. The resinous polymers of vinyl chloride include homopolymeric polyvinyl chloride, 95/5 vinyl chloride/vinyl acetate copolymers, etc. The plasticizers can be used in a concentration of from 5 to 300 parts by weight per each 100 parts by weight resinous polymer of vinyl chloride as the sole plasticizer or together with other plasticizers such as dioctyl phthalate, trioctyl phosphate, epoxidized glyceride oils, etc.

The adamantane polyphenyl carboxylic acid compounds containing two acyl moieties can be used to produce high molecular weight condensation polymers, such as polyesters or polyamides. These can be made by condensing at least one of the novel polyacyl compounds with an organic compound providing two reactive groups derived from either a polyhydric alchol, a polyamine, a polyisocyanate or a polyisothiocyanate. These polyols, polyamines, polyisocyanates, or polythiocyanates can be saturated or unsaturated aromatic or aliphatic, straight or branched chain, substituted or unsubstituted.

In general, the highly polymeric essentially linear condensation polymers are resinous polymers consisting essentially of recurring units of a polyacyl radical of an adamantane polyphenylcarboxylic acid wherein said resinous polymer is of the structural formula

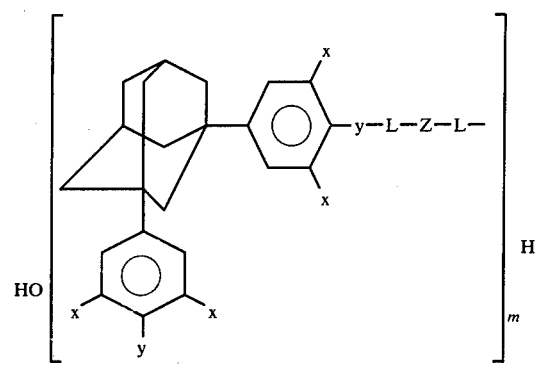

wherein x and y are selected from the group consisting of

and —H, n is a whole number of 1 to 4, L is selected from the group consisting of

and —O— radials, Z is selected from the group consisting of aliphatic moieties and aromatic moieties, m is a number of said recurring units wherein the said resinous polymer has an inherent viscosity of at least 0.20 deciliters per gram (dl/g) in a 60/40 phenol-tetrachloroethane solvent at 30° C.

For purposes of this invention, the term "aromatic moiety" is defined as including aromatic radicals characterized by at least one benzene ring, i.e., the six-carbon ring of benzene or the condensed six-carbon rings of the other aromatic radicals such as naphthylene, phenanthrylene, anthrylene, etc. The term "aromatic moiety" is further defined as including radicals containing two benzene rings joined by a group such as a methylene group, ether, sulfone, sulfide group, etc. Examples of these radicals are phenylene, biphenylene, diphenylene ether, diphenylene methane, diphenylene sulfone, and diphenylene sulfide. One or more hydrogens of the aromatic nucleus can be replaced by non-reactive radical groups such as lower alkyls, halogens and nitro radicals. For purposes of this invention, the term "alkylene" is defined as including groups having 2 to 20 carbon atoms in the alkylene chain.

The polyesters of this invention comprise a polyhydroxy component comprising one or more polyhydric alcohols (diols, triols, etc.) and a polycarboxylic acid component comprising one of the adamantane polyphenyl carboxylate components. The preferred polyesters of this invention are essentially linear and comprise units of alkylene glycols containing 2 to 10 carbon atoms and adamantane carboxylate moieties.

The polyhydric alcohols useful in this invention include alkylene glycols containing from about 2–12 carbon atoms, such as ethylene glycol, propylene glycol, 1,2-propylene glycol, butylene glycol, hexamethylene glycol, dodecamethylene glycol, etc.; aromatic polyhydric alcohols, such as hydroquinone, resorcinol, Bisphenol A, etc.; cycloaliphatic glycols such as 1,4-dimethylol cyclohexane, dimethylol cyclobutane, etc.; polyoxyalkylene glycols, such as polyoxyethylene glycols, polyoxypropylene glycols, block copolymers of polyethylene and polypropylene glycol, polytetramethylene glycols, etc.; neopentyl glycol, polyhydric alcohols having three or more hydroxy groups, such as 1,1,1-trimethylol ethane, 1,1,1-trimethylol propane, pentaerythritol, sorbitol, reaction products of the aforesaid polyhydric alcohols having a functionality of three or more with alkylene oxides (ethylene oxide or propylene oxide) such as those sold for use in the production of flexible polyurethane foams, etc.

Broadly speaking, the polyesters of this invention can be made by reacting polyhydric alcohol with the appropriate polycarboxylic acid or lower alkyl (preferably methyl) ester of the polycarboxylic acid. A plurality of ester-forming derivatives of polyhydric alcohols can be employed, i.e., a derivative of the alcohol containing functional groups equivalent to the hydroxyl groups in their ability to react with carboxyl groups. Thus, an alcohol can be employed in the form of an epoxide, and/or ester of the alcohol with acetic acid or other lower aliphatic acid may be used.

A convenient method for preparing the polyesters of this invention comprises reacting the dimethyl ester of the dicarboxylic acid or acid with an excess of the polyhydric alcohol, approximately 1.1 to 2.5 moles of alcohol per mole of ester, preferably about 1.5 to 2.1 moles of alcohol per mole of ester. The ester interchange reaction can be carried out at atmospheric pressure but higher or lower pressure can be used if desired. A range is usually from 0.1 to ten atmospheres. Temperature range is usually from 90° C. to 325° C. Following the ester interchange reaction, in which methanol is removed as a by-product, heating is continued at an increased temperature to bring about polycondensation. Small amounts of catalysts are usually added to facilitate the reaction, manganous acetate, calcium acetate, and sodium methoxide being typical ester interchange catalysts and antimony trioxide, dibutyl tin maleate, and zinc acetate being suitable polycondensation catalysts. Litharge, sodium hydrogen hexabutoxytitanate and the tetra-alkyl titanates, such as tetra-isopropyl titanate, are examples of catalysts which can be used for both the ester interchange and the polycondensation steps. Normally, the polycondensation reaction is continued until a degree of polymerization is achieved corresponding to an inherent viscosity of approximately at least 0.20 deciliters per gram (dl/g) in a 60/40 phenol-tetrachloroethane solvent at 30° C.

To achieve a higher degree of polymerization, the product of the polycondensation reaction is allowed to cool to room temperature, about 20° to 25° C., forming a solid material. The solid is ground to flake, following which the flake is heated below its melting point in a stream of inert gas to achieve said phase polycondensation.

The essentially linear polycarbonamides of this invention can be viewed as polyphenyl dicarboxamides having arylene and/or alkylene groups joining the amide groups of the polymer. One or more of the alkylene or arylene groups can be joined by one or more heteroatoms (—O—,

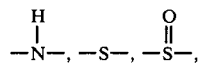

etc.) as is common in this art.

Suitable alkylene groups containing 2 to 24 carbon atoms include ethylene, butylene, trimethylene, hexamethylene, octamethylene, dodecamethylene,

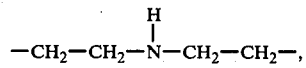

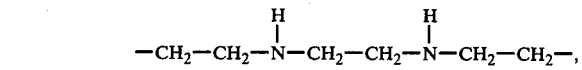

tetracosene, etc. Suitable arylene groups containing 6 to 24 carbon atoms include paraphenylene, orthophenylene, N,N-diphenyleneamine, oxydiphenylene, etc.

The high molecular weight polyamides can be prepared by well-known methods. These methods include reacting a dicarboxylic acid or its derivatives such as acid chlorides with alkylene and arylene diamines, diisocyanates, diisothiocyanates and their derivatives. For example, polyamides can be prepared from the free acid (1,3-di(4-carboxyphenyl)adamantane) and difunctional nitrogen-containing compounds such as diphenylmethane-4,4'-diisocyanate, diphenylether-4,4'-diisocyanate, 4,4'-diaminodiphenylmethane, paraphenylene diamine, etc.

In somewhat greater detail, the dicarboxylic acid can be reacted with an excess of the arylene diamine, diisocyanate, or diisothiocyanate (1.1 to 2.5 moles of reactant per mole of acid, preferably about 1.5 to 2.1 moles of reactant per mole of acid.) The reaction can be carried out at atmospheric pressure but higher or lower pressure can be used if desired. The temperature is usually from about 90° to 325° C. Small amounts of catalyst can be added to facilitate the reaction. Normally, the reaction is continued until the desired degree of polymerization is achieved.

Accordingly, the invention comprises a polyphenylcarboxylic acid adamantane compound exemplified by a 1,3-diphenylcarboxylic acid adamantane compound wherein the two phenyl carboxylic acid moieties are the same and are selected from the group consisting of

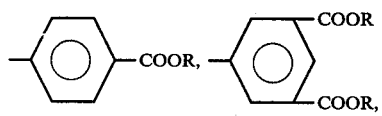

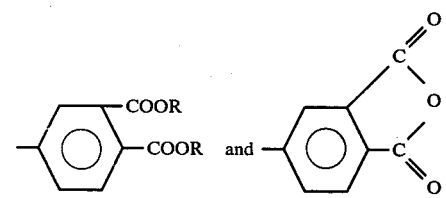

where R is hydrogen or a alkyl group of 1 to 4 carbon atoms. Among others, the said compound comprises 1,3-di(4-carboxylphenyl)adamantane; 1,3-di(3,4-dicarboxyphenyl)adamantane; 1,3-di(3,5-dicarboxyphenyl)adamantane; 1,3-di(3,4-dicarboxyphenyl)adamantane dianhydride and the alkyl esters of the said compounds, the alkyl chain being a lower alkyl group of 1 to 4 carbon atoms. Among others, the alkyl ester of said compounds comprises 1,3-di(4-carbomethoxyphenyl)adamantane and 1,3-di(3,5-dicarbomethoxyphenyl)adamantane.

The polyphenylcarboxylic acid adamantane compound can be prepared by oxidizing the reaction product of a polybromoadamantane and an alkyl benzene in the presence of sodium dichromate dihydrate. The dianhydride is prepared in one method by heating the adamantane or the diacid with acetic anhydride. The ester is prepared by heating the acid in the presence of the desired alkyl alcohol of 1 to 4 carbon atoms chain length with small amounts of a suitable esterification catalyst if such is needed. A suitable catalyst is sulfuric acid. The acyl chloride can also be the source of the ester.

The invention also comprises a high molecular weight polyester, specifically of the 1,3-diphenylcarboxylic acid adamantane compound which comprises a polyhydroxy component comprising an alkylene glycol moiety containing 2 to 12 carbon atoms and the 1,3-diphenylcarboxylate moieties. In one example, the said polyhydroxy component comprises ethylene glycol moieties. The polyester reaction intermediate is prepared by refluxing under nitrogen the 1,3-di(4-carbomethoxyphenyl)adamantane with the polyhydroxy compound with a catalyst comprising calcium acetate for a period of 15 minutes. After the removal of excess polyhydroxy compound and the alcohol formed by distillation, the reaction mixture is ground with antimony trioxide as catalyst, and heated for a period of about 2 hours at a temperature of about 220° C. to 275° C. A nitrogen stream is passed through the melted material during the entire polymerization.

In summary, the invention comprises adamantane polyphenylcarboxylic acid compounds wherein the adamantane moiety is substituted in two to four bridgehead positions with phenylacyl moieties with carboxy groups in the 3, 4, 5 positions on the phenyl rings. The invention also comprises a process for preparing the adamantane polyphenylcarboxylic acid compounds wherein the carboxy groups are in the 3, 4, 5 positions on the phenyl rings. The process comprises oxidizing the reaction product of a polybromoadamantane and an alkyl benzene having up to two alkyl groups ortho or meta to each other in a liquid phase oxidation at a temperature within the range of 75° to 300° C., the oxidizing agent being selected from the group consisting of sodium dichromate and molecular oxygen catalyzed by the conjoint presence of a transition metal and bromine solubilized in an organic acid solvent. The invention also comprises a polyester of the said adamantane polyphenylcarboxylic acid compound of a polycarboxylic acid component and a polyhydroxy component wherein the polycarboxylic acid component comprises 1,3-diphenyl carboxylate moieties on the bridgehead positions of 1, 3, 5 and 7 of the adamantane nucleus and the polyhydroxy component comprises an alkylene glycol moiety containing 2 to 12 carbon atoms. The invention also comprises a polyamide of the said adamantane polyphenylcarboxylic acid compound of a polycarboxylic acid component and a difunctional nitrogen-containing component of a suitable alkylene group containing 2 to 24 carbon atoms and/or arylene group containing 6 to 24 carbon atoms.

In order to facilitate a clear understanding of the invention, the following specific embodiments are described in detail. It should be understood, however, that the detailed expositions of the application of the invention, while indicating preferred embodiments, are given by way of illustration only since various changes and modifications within the spirit and scope of the invention will become apparent to those skilled in the art from this detailed description.

EXAMPLE I

This example illustrates the production of di-methylphenyl adamantane derivatives and conversion of these derivatives into mono acids and the methyl esters.

Three grams of 1,3-dibromoadamantane were dissolved in 60 ml of toluene and added dropwise over 30 minutes to a stirred mixture of 0.567 grams of ferric chloride acid in 450 ml of toluene heated to 50° C. in a small round-bottomed three-necked flask equipped with a dropping funnel, thermometer, magnetic stirrer and electric heating mantle. The solution was heated for one hour with stirring to 50° C. The reaction mixture was hydrolyzed by the addition of 200 ml water. The organic phase was separated, dried with anhydrous magnesium sulfate, and concentrated under reduced pressure to give 3.14 grams of 1,3-di(4-methylphenyhl)adamantane (crude yield 99%). The white crystals were recrystallized from ether to give crystals with a melting point of 144°-146° C. The analysis was verified by nuclear magnetic resonance (NMR) and mass spectrometry.

The preparation of 1,3-di(4-methylphenyl)adamantane was repeated using a diol adamantane. Ten grams of 1,3-dihydroxyadamantane, prepared from 1,3-dibromoadamantane according to the method of Stetter et al., Chem. Ber., 93, 1366 (1960), were added to a stirred mixture of 500 ml toluene containing 70 ml reagent grade sulfuric acid (95–99% $H_2SO_4$) and 15 ml water. The reaction mixture was maintained at 40° C. with stirring overnight. The organic layer containing the reaction product was separated, washed with water and dried with anhydrous magnesium sulfate. Concentration of the toluene solution yielded 1,3-di(4-methylphenyl)adamantane, 11 grams, M.P. 145°-146° C. (Crude yield 59%)

OXIDATION OF 1,3-DI(4-METHYLPHENYL)ADAMANTANE

A mix of 7.47 grams of cobalt acetate tetrahydrate, 3.27 grams of cobalt bromide hexahydrate, and 4 grams of 1,3-di(4-methylphenyl)adamantane in 300 ml glacial acetic acid were allowed to reflux at a temperature of 120° C., in a three-necked round-bottomed flask equipped with an oxygen bubbler, a refluxing column, a magnetic stirrer, a thermometer and a heating mantle. Oxygen was introduced at 0.1 SCFH. Six grams 1,3-di(4-methylphenyl)adamantane were then added to this solution over a period of three hours. The reaction mixture was allowed to reflux for an additional 28 hours. 100 ml. of water were added to the cooled reaction mixture, and the resulting precipitate was filtered off. The filter cake was washed with water and dissolved in dilute sodium hydroxide. The basic solution was extracted with chloroform to remove non-acidic components. Dilute hydrochloric acid was added to acidify the solution. The precipitated crystals were filtered and dried to give 10.7 grams 1,3-di(4-carboxyphenyl)adamantane, M.P. 304°-306° C.

ESTERIFICATION OF 1,3-DI(4-CARBOXYPHENYL)ADAMANTANE

The quantity 0.5 grams 1,3-di(4-carboxyphenyl)adamantane was esterified by refluxing for two hours in 30 ml of methanol containing 0.5 ml of concentrated sulfuric acid. The methanol was distilled and the residue dissolved in ether. The ether solution was washed with water, dried over anhydrous magnesium sulfate and concentrated to give 0.44 grams of 1,3-di(4-carbomethoxyphenyl)adamantane (crude yield 59%). The white crystals were recrystallized from methanol to give crystals with a melting point of 164°–165° C. The analysis was verified by NMR and mass spectra. Calculated analysis for $C_{26}H_{28}O_4$ is: C, 77.19; H, 6.98; found: C, 77.03; H, 7.14.

EXAMPLE II

This example illustrates the production of di-(dimethylphenyl)adamantane derivatives and conversion of these derivatives into tetra-acids and their methyl esters.

A mixture of 3.0 grams of 1,3-dibromoadamantane and 0.057 grams of ferric chloride in 440 ml of meta-xylene was refluxed for one hour and worked up according to the procedure of Example I. Yield was 3.17 grams (92% yield) of 1,3-di(3,5-dimethylphenyl)adamantane, melting point 231°–232° C. The analysis was verified by NMR. Calculated analysis for $C_{26}H_{32}$ was: C, 90.63; H, 9.37; found: C, 90.60; H, 9.25.

OXIDATION OF 1,3-DI(3,5-DIMETHYLPHENYL)ADAMANTANE 2.59g of sodium dichromate dihydrate and 0.5g of 1,3-di(3,5-dimethylphenyl)adamantane were mixed in 50 ml of water in a stainless steel rocking autoclave. The temperature of the reacting mixture was held at 250° C. for 18 hours at a pressure of 560 psig. After the 18 hours of reaction, the reaction mixture was cooled and filtered to remove the chromium oxide. The aqueous solution was acidified with dilute hydrochloric acid and the resulting precipitate was separated by filtration, yielding 0.25 grams of the acid, M.P. 320°–330° C. dec.

ESTERIFICATION OF 1,3-DI(3,5-DICARBOXYPHENYL)ADAMANTANE

The 0.25 grams of acid prepared as above was esterified by mixing the acid in 25 ml of methanol containing 1 ml of concentrated $H_2SO_4$ and allowing the mixture to reflux for 2½ hours. The methanol was distilled and the residue was dissolved in ether. The ether solution was washed with water, dried over anhydrous magnesium sulfate and distilled to yield 0.22 grams of white crystals. The white crystals were recrystallized from methanol to give crystals with a melting point of 224°–226° C. Overall yield was 28%. The analysis was verified by NMR, infrared analysis and mass spectrometry.

EXAMPLE III

This example illustrates the production of di-(dimethylphenyl)adamantane derivatives and conversion of these derivatives into a dianhydride.

The quantity 0.3 grams of 1,3-dibromoadamantane was mixed with 0.057 grams of ferric chloride in 50 ml of ortho-xylene. The mixture was allowed to reflux for 18 hours. The reaction mixture was worked up according to the procedure of Example I to give 0.25 grams (72% yield) of white crystals, melting point 162°–163° C. The NMR spectra was consistent with that of 1,3-di(3,4-dimethylphenyl)adamantane. Calculated analysis for $C_{26}H_{32}$ was: C, 90.63; H, 9.37; found: C, 90.23; H, 9.24.

The above procedure was repeated to obtain a total of approximately 20g of 1,3-di(3,4-dimethylphenyl)adamantane.

OXIDATION OF 1,3-DI(3,4-DIMETHYLPHENYL)ADAMANTANE

A mixture of 14.19g of cobalt acetate tetrahydrate, 3.82g cobalt bromide hexahydrate dissolved in 570 ml of glacial acetic acid containing 3.0 grams 1,3-di(3,4-dimethylphenyl)adamantane was allowed to reflux. An oxygen gas flow of 2.5 cubic feet per hour was bubbled through the refluxing mixture. Over a period of 7 hours, an additional 16.6g of 1,3-di(3,4-dimethylphenyl)adamantane were added to the refluxing mixture. The reaction mixture was refluxed for an additional 48 hours, during which the oxygen flow was maintained at a constant 2.5 cubic feet/hour. After the 48 hours, the reaction mixture was allowed to cool. Excess acetic acid was boiled off to concentrate the reaction mixture to 100 ml. 300 ml of water were added and the mixture was filtered.

The resulting filter cake was dissolved in dilute sodium hydroxide. The filtrate was extracted with ethyl acetate. The ethyl acetate extract was concentrated to dryness and dissolved in sodium hydroxide. The resulting solution was combined with the basic solution derived from the filter cake. The basic solution was then extracted with ether which, upon evaporation, gave 0.2 grams of non-acidic material. Acidification of the basic solution with dilute hydrochloric acid followed by an ethyl acetate extraction yielded 20.4 grams of acid. The dry acid was allowed to reflux in 100 ml of acetic anhydride for 2 hours. The acetic anhydride was removed by distillation and the residue was recrystallized from ethyl acetate to give 9.5 grams of crude dianhydride (overall yield 37%).

Further recrystallization from acetone gave 6.0 grams of white crystals, melting point 211°–212° C. The analysis was verified by NMR and infrared spectra. Calculated analysis for $C_{26}H_{22}O_6$ is: C, 72.54; H, 5.15; found: C, 72.65; H, 4.73.

EXAMPLE IV

This example illustrates the preparation of diphenylcarboxylic acid compounds wherein two of the bridgehead positions are occupied by alkyl groups.

A quantity of 5.0 grams (0.025 moles) of 1,3-dimethyl-5,7-dihydroxy adamantane was added to 250 ml of toluene with 35 ml of 95% sulfuric acid and 8 ml of water at 50° C. in a round-bottomed flask, with stirring over a period of two hours. The mixture was then stirred at 50° C. for three hours. The organic layer was separated and washed with sodium chloride solution. The toluene solution was dried over sodium sulfate and concentrated to 8.2 grams (95% yield) of a pale yellow oil. Infrared, mass spectrometry and NMR analyses showed the material was 1,3-di(4-methylphenyl)-5,7-dimethyladamantane.

OXIDATION OF 1,3-DI(4-METHYLPHENYL)(-5,7-DIMETHYL)ADAMANTANE

In the method of Example III, 2.0 grams of 1,3-di(4-methylphenyl)-5,7-dimethyl adamantane were allowed to reflux with 300 ml of acetic acid containing 5.26 grams (0.022 moles) cobalt acetate tetrahydrate and, 2.39 grams cobalt bromide hexahydrate. An oxygen gas flow of 1 cubic foot per hour was bubbled through the refluxing mixture. Over a period of 6 hours, 5.39 grams of 1,3-di(4-methylphenyl)-5,7-dimethyl adamantane were added for a total of 7.39 grams. The reaction mixture was allowed to reflux an additional 28 hours. The reaction mixture was then mixed with water and the mixture was filtered. The resulting filter cake was dissolved in dilute sodium hydroxide. The filtrate was extracted with ether. The ether extracts was evaporated, but gave no residue. The basic solution was acidified with hydrochloric acid followed by an ethyl acetate extraction. Drying and concentration of the ethyl acetate gave 7.12 grams of 1,3-di(4-carboxyphenyl)-5,7-dimethyl adamantane (82% yield), M.P. 252°–255° C.

Esterification of 3.11g of 1,3-di(4-carboxyphenyl)-5,7-dimethyl adamantane with sulfuric acid as catalyst in 80 ml of methanol followed. Drying and concentration gave 3.25 grams of the diester. The analysis was verified by infrared and mass spectrometric analyses.

EXAMPLE V

This example illustrates the preparation of a polyester from 1,3-di(4-carbomethoxyphenyl)adamantane.

The quantities of 5.2g (0.0129 moles) of 1,3-di(4-carbomethoxyphenyl)adamantane, and 2.07g (0.033 moles) of ethylene glycol were mixed with 0.009 grams calcium acetate in a 100 ml three-necked round-bottomed flask and allowed to reflux at 180° C. for 15 minutes. The flask was equipped with a nitrogen gas inlet tube, a thermometer, a condenser, and a magnetic stirrer. The temperature was then dropped to 160° C. and the reaction mixture was distilled over a period of one hour at a pressure of 0.3mm Hg to remove the methanol formed, along with the remaining ethylene glycol. The hot residue was cooled in an evaporating dish. Yield was 5.0 grams of reaction intermediate.

The 5.0 grams of reaction intermediate were ground with 0.005 grams antimony trioxide. The ground mixture was placed in a polymerization tube and heated for ½ hour at 220° C. at one atmosphere under nitrogen gas. A vacuum of 0.15mm Hg was applied; the temperature was increased to and held at 275° C. for 1½ hours. The amorphous polyester which resulted was cooled to room temperature and removed from the tube.

The polyester had a glass transition temperature of 138° C. and did not begin to decompose during thermal gravimetric analysis until heated beyond 350° C. The polyester flowed at 240° C.

What is claimed is:

1. A polyphenylcarboxylic acid adamantane compound of the general formula

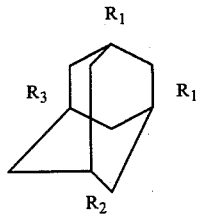

wherein $R_1$ is selected from the group consisting of

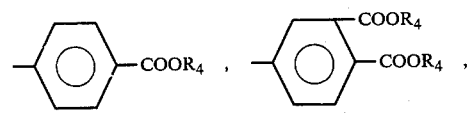

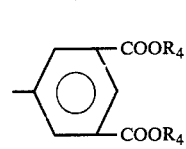 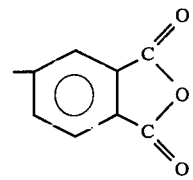

$R_2$ and $R_3$ are individually selected from the group consisting of hydrogen, an alkyl radical of 1 to 4 carbon atoms, a phenyl radical, a biphenyl radical, and a naphthyl radical, $R_4$ is hydrogen or an alkyl group of 1 to 24 carbon atoms.

2. The compound of claim 1 which consists of 1,3-di(4-carboxyphenyl) adamantane.

3. The compound of claim 1 which consists of 1,3-di(3,4-dicarboxyphenyl) adamantane.

4. The compound of claim 1 which consists of 1,3-di(3,5-dicarboxyphenyl) adamantane.

5. The compound of claim 1 which consists of 1,3-di(3,4-dicarboxyphenyl) adamantane dianhydride.

6. The compound of claim 1 which consists of 1,3-di(4-carboxyphenyl)-5,7-dimethyl adamantane.

7. The compound of claim 1 which consists of the dimethyl ester 1,3-di(4-carbomethoxyphenyl) adamantane.

8. The compound of claim 1 which consists of the tetramethyl ester 1,3-di(3,4-di-carbomethoxyphenyl) adamantane.

9. The compound of claim 1 which consists of the tetramethyl ester 1,3-di(3,5-dicarbomethoxyphenyl) adamantane.

10. The compound of claim 1 which consists of the dimethyl ester 1,3-di(4-carbomethoxyphenyl)-5,7-dimethyl adamantane.

11. A process for preparing adamantane polyphenylcarboxylic acid compounds, wherein the carboxy groups are in the 3, 4, 5 positions on the phenyl rings which comprises oxidizing the reaction product of a polybromoadamantane and an alkyl benzene in a liquid phase oxidation at a temperature within the range of about 75° to 300° C., the oxidizing agent being selected from the group consisting of sodium dichromate, potassium dichromate, ammonium dichromate, and molecular oxygen.

12. The process of claim 11 wherein the said alkyl groups comprise methyl groups.

13. The process of claim 11 wherein the said oxidizing agent is sodium dichromate and the said temperature range is from about 230° to 300° C.

14. The process of claim 11 wherein the said oxidizing agent is molecular oxygen catalyzed by the conjoint presence of a transition metal and bromine solubilized in an organic acid solvent, the said temperature range being from about 100° to 150° C.

15. The process of claim 14 wherein the said transition metal is cobalt and the said organic acid is acetic acid.

16. A resinous polymer consisting essentially of recurring units of a polyacyl radical of an adamantane polyphenylcarboxylic acid wherein the said resinous polymer is of the structural formula:

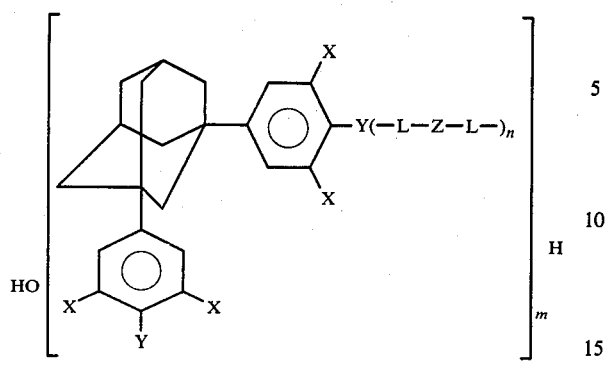

wherein X and Y are selected from the group consisting of

and —H, n is a whole number of 1 to 4, L is selected from the group consisting of

and —O— radicals, Z is selected from the group consisting of aliphatic moieties of 2 to 20 carbon atoms and aromatic moieties selected from the group consisting of one benzene ring and the condensed rings of naphthylene, phenanthrylene and anthrylene, m is a number of said recurring units wherein the said resinous polymer has an inherent viscosity of at least 0.20 dl/g in a 60/40 phenol-tetrachloroethane solvent at 30° C.

17. The polymer of claim 16 wherein the said aliphatic moiety is an ethyl group.

18. The polymer of claim 16 wherein said aromatic moieties are selected from the group consisting of phenylene, biphenylene, diphenylene ether, diphenylene methane, diphenylene sulfone, diphenylene sulfide, naphthylene, phenanthrylene and anthrylene moieties.

19. The polymer of claim 18 wherein said aromatic moieties comprise substituted moieties, said substitutions selected from the group of radicals consisting of lower alkyls, halogens, and nitro radicals.

20. The polymer of claim 16 wherein Z comprises ethylene.

21. The polymer of claim 16 wherein Z comprises butylene.

22. The polymer of claim 16 wherein LZL is

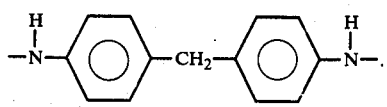

23. The polymer of claim 16 wherein LZL is

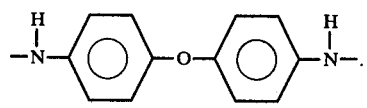

24. The polymer of claim 16 wherein X is—H, Y is

and the said polyacyl radical is derived from 1,3-di(4-carboxyphenyl) adamantane.

25. The polymer of claim 16 wherein X is—H, Y is

and the said polyacyl radical is derived from 1,3-di(3,4-dicarboxyphenyl) adamantane.

26. The polymer of claim 16 wherein X is—H, Y is

and the said polyacyl radical is derived from 1,3-di(3,5-dicarboxyphenyl) adamantane.

27. The polymer of claim 16 wherein X is—H, Y is

and the said polyacryl radical is derived from 1,3-di(4-carboxyphenyl)-5,7-dimethyl adamantane.

* * * * *

UNITED STATES PATENT OFFICE
CERTIFICATE OF CORRECTION

Patent No. 4,142,036          Dated February 27, 1979

Inventor(s) Allen I. Feinstein and Ellis K. Fields

It is certified that error appears in the above-identified patent and that said Letters Patent are hereby corrected as shown below:

| Patent Column | Line | |
|---|---|---|
| 4 | 11 | "product" should be --produce-- |
| 4 | 31 | "dicharomate" should be --dichromate-- |
| 4 | 41 | "of any" should be --at any-- |
| 6 | 31 | "radials" should be --radicals-- |
| 7 | 57 | "said phase" should be --solid phase-- |
| 13 | 8 | "extracts" should be --extract-- |
| 16 | 46 | "polyacryl" should be --polyacyl-- |

Signed and Sealed this

Twelfth Day of August 1980

[SEAL]

Attest:

SIDNEY A. DIAMOND

Attesting Officer      Commissioner of Patents and Trademarks